United States Patent [19]

Schuster et al.

[11] Patent Number: 5,169,766
[45] Date of Patent: Dec. 8, 1992

[54] AMPLIFICATION OF NUCLEIC ACID MOLECULES

[75] Inventors: David M. Schuster, Poolesville; Mark S. Berninger, Gaithersburg, both of Md.

[73] Assignee: Life Technologies, Inc., Gaithersburg, Md.

[21] Appl. No.: 715,603

[22] Filed: Jun. 14, 1991

[51] Int. Cl.$^5$ .................. C12P 19/34; C12N 15/11
[52] U.S. Cl. ..................... 435/91; 536/27; 435/6; 435/193; 435/194
[58] Field of Search .......... 435/91, 172.3, 172.1, 435/6, 193, 194; 536/27; 935/16, 77

[56] References Cited

U.S. PATENT DOCUMENTS

| | | | |
|---|---|---|---|
| 4,582,788 | 4/1986 | Erlich | 435/6 |
| 4,683,194 | 7/1987 | Saiki et al. | 435/6 |
| 4,683,195 | 7/1987 | Mullis et al. | 435/6 |
| 4,985,359 | 1/1991 | Oberbäumer | 435/91 |

FOREIGN PATENT DOCUMENTS

| | | |
|---|---|---|
| 329822 | 8/1989 | European Pat. Off. |
| 0397269 | 11/1990 | European Pat. Off. |
| WO88/10315 | 12/1988 | PCT Int'l Appl. |
| WO89/06700 | 7/1990 | PCT Int'l Appl. |

OTHER PUBLICATIONS

Higuchi (1989), in DNA Amplification Using the PCR (Macmillan), pp. 61–68.
Strategene catalog (1989), pp. 55, 61.
Kwoh, D. et al., *Proc. Natl. Acad. Sci.* (U.S.A.) 86:1173 (1989).
Milligan, J. F. et al., *Nucleic Acids Res.* 15:8783–8798 (1987).
Mullis, K. et al., *Cold Spring Harbor Symp. Quant. Biol.* 51:263–273 (1986).
Mullis, K. B. et al., *Met. Enzymol.* 155:335–350 (1987).
Saiki, R. K. et al., (*Bio/Technology* 3:1008–1012 (1985)).
Sharmeen, L. et al., *Nucleic Acids Res.* 15:6705–6711 (1987).
Wu, D. Y. et al., *Genomics* 4:560 (1989).

*Primary Examiner*—Richard A. Schwartz
*Assistant Examiner*—James Ketter
*Attorney, Agent, or Firm*—Jeffrey I. Auerbach

[57] ABSTRACT

A method for amplifying a nucleic acid molecule which employs a proto-promoter-containing nucleic acid molecule having a blocked 3' terminus. The invention also includes kits containing reagents for conducting the method.

13 Claims, 4 Drawing Sheets

AMPLIFICATION OF NUCLEIC ACID MOLECULES

FIELD OF THE INVENTION

The present invention is in the field of recombinant DNA technology. This invention is directed to a process for amplifying a nucleic acid molecule, and to the molecules employed and produced through this process.

BACKGROUND OF THE INVENTION

Assays capable of detecting the presence of a particular nucleic acid molecule in a sample are of substantial importance in forensics, medicine, epidemiology and public health, and in the prediction and diagnosis of disease. Such assays can be used, for example, to identify the causal agent of an infectious disease, to predict the likelihood that an individual will suffer from a genetic disease, to determine the purity of drinking water or milk, or to identify tissue samples. The desire to increase the utility and applicability of such assays is often frustrated by assay sensitivity. Hence, it would be highly desirable to develop more sensitive detection assays.

Nucleic acid detection assays can be predicated on any characteristic of the nucleic acid molecule, such as its size, sequence, and, if DNA, susceptibility to digestion by restriction endonucleases, etc. The sensitivity of such assays may be increased by altering the manner in which detection is reported or signaled to the observer. Thus, for example, assay sensitivity can be increased through the use of detectably labeled reagents. A wide variety of such labels have been used for this purpose. Kourilsky et al. (U.S. Pat. No. 4,581,333) describe the use of enzyme labels to increase sensitivity in a detection assay. Radioisotopic labels are disclosed by Falkow et al. (U.S. Pat. No. 4,358,535), and by Berninger (U.S. Pat. No. 4,446,237). Fluorescent labels (Albarella et al., EP 144914), chemical labels (Sheldon III et al., U.S. Pat. No. 4,582,789; Albarella et al., U.S. Pat. No. 4,563,417), modified bases (Miyoshi et al., EP 119448), etc. have also been used in an effort to improve the efficiency with which detection can be observed.

Although the use of highly detectable labeled reagents can improve the sensitivity of nucleic acid detection assays, the sensitivity of such assays remains limited by practical problems which are largely related to non-specific reactions which increase the background signal produced in the absence of the nucleic acid the assay is designed to detect. Thus, for some applications, such as for the identification of a pure culture of a bacteria, etc., the concentration of the desired molecule will typically be amenable to detection, whereas, for other potential applications, the anticipated concentration of the desired nucleic acid molecule will be too low to permit its detection by any of the above-described assays.

In response to these impediments, a variety of highly sensitive methods for DNA amplification have been developed.

One method for overcoming the sensitivity limitation of nucleic acid concentration is to selectively amplify the nucleic acid molecule whose detection is desired prior to performing the assay. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., *Molecular Cloning (A Laboratory Manual)*, Cold Spring Harbor Laboratory, 1982, etc.

Another method for amplifying a nucleic acid molecule is by template directed extension. In such a method, the nucleic acid molecule is used as a template for extension of a nucleic acid primer in a reaction catalyzed by polymerase. For example, Panet and Khorana (*J. Biol. Chem.* 249:5213–5221 (1974) which reference is incorporated herein by reference) demonstrated the replication of deoxyribopolynucleotide templates bound to cellulose. Kleppe et al (*J. Mol. Biol* 56:341–361 (1971) which reference is incorporated herein by reference) disclosed the use of double- and single-stranded DNA molecules as templates for the synthesis of complementary DNA.

Such methods form the basis of the "polymerase chain reaction" ("PCR"), which is among the most widely used methods of DNA amplification (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194), which references are incorporated herein by reference). PCR achieves the amplification of a specific nucleic acid sequence using two oligonucleotide primers complementary to regions of the sequence to be amplified. Extension products incorporating the primers then become templates for subsequent replication steps.

The polymerase chain reaction provides a method for selectively increasing the concentration of a nucleic acid molecule having a particular sequence even when that molecule has not been previously purified and is present only in a single copy in a particular sample. The method can be used to amplify either single or double stranded DNA. The essence of the method involves the use of two oligonucleotides to serve as primers for the template-dependent, polymerase mediated replication of the desired nucleic acid molecule.

The precise nature of the two oligonucleotide primers of the PCR method is critical to the success of the method. As is well known, a molecule of DNA or RNA possesses directionality, which is conferred through the 5'→3' linkage of the sugar-phosphate backbone of the molecule. Two DNA or RNA molecules may be linked together through the formation of a phosphodiester bond between the terminal 5' phosphate group of one molecule and the terminal 3' hydroxyl group of the second molecule. Polymerase dependent amplification of a nucleic acid molecule proceeds by the addition of a 5' nucleoside triphosphate to the 3' hydroxyl end of a nucleic acid molecule. Thus, the action of a polymerase extends the 3' end of a nucleic acid molecule. These inherent properties are exploited in the selection of the two oligonucleotide primers of the PCR. The oligonucleotide sequences of the two primers of the PCR method are selected such that they contain sequences identical to, or complementary to, sequences which flank the sequence of the particular nucleic acid molecule whose amplification is desired. More specifically, the nucleotide sequence of the "first" primer is selected such that it is capable of hybridizing to an oligonucleotide sequence located 3' to the sequence of the desired nucleic acid molecule, whereas the nucleotide sequence of the "second" primer is selected such that it contains a nucleotide sequence identical to one present 5' to the sequence of the desired nucleic acid molecule Both primers possess the 3' hydroxyl groups which are necessary for enzyme mediated nucleic acid synthesis.

In the polymerase chain reaction, the reaction conditions are cycled between those conducive to hybridization and nucleic acid polymerization, and those which result in the denaturation of duplex molecules. In the first step of the reaction, the nucleic acids of the sample are transiently heated, and then cooled, in order to denature any double stranded molecules which may be present. The "first" and "second" primers are then added to the sample at a concentration which greatly exceeds that of the desired nucleic acid molecule. When the sample is incubated under conditions conducive to hybridization and polymerization, the "first" primer will hybridize to the nucleic acid molecule of the sample at a position 3' to the sequence of the desired molecule to be amplified. If the nucleic acid molecule of the sample was initially double stranded, the "second" primer will hybridize to the complementary strand of the nucleic acid molecule at a position 3' to the sequence of the desired molecule which is the complement of the sequence whose amplification is desired. Upon addition of a polymerase, the 3' ends of the "first" and (if the nucleic acid molecule was double stranded) "second" primers will be extended. The extension of the "first" primer will result in the synthesis of a DNA molecule having the exact sequence of the complement of the desired nucleic acid. Extension of the "second" primer will result in the synthesis of a DNA molecule having the exact sequence of the desired nucleic acid.

The PCR reaction is capable of exponential amplification of specific nucleic acid sequences because the extension product of the "first" primer contains a sequence which is complementary to a sequence of the "second" primer, and thus will serve as a template for the production of an extension product of the "second" primer. Similarly, the extension product of the "second" primer, of necessity, contain a sequence which is complementary to a sequence of the "first" primer, and thus will serve as a template for the production of an extension product of the "first" primer. Thus, by permitting cycles of hybridization, polymerization, and denaturation, a geometric increase in the concentration of the desired nucleic acid molecule can be achieved. Reviews of the polymerase chain reaction are provided by Mullis, K. B. (*Cold Spring Harbor Symp. Quant. Biol.* 51:263–273 (1986)); Saiki, R. K., et al. (*Bio/Technology* 3:1008–1012 (1985)); and Mullis, K. B., et al. (*Met. Enzymol.* 155:335–350 (1987), which references are incorporated herein by reference).

PCR technology is useful in that it can achieve the rapid and extensive amplification of a polynucleotide molecule. However, the method requires the preparation of two different primers which hybridize to two oligonucleotide sequences flanking the target sequence. The concentration of the two primers can be rate limiting for the reaction. Although it is not essential that the concentration of the two primers be identical, a disparity between the concentrations of the two primers can greatly reduce the overall yield of the reaction.

A further disadvantage of the PCR reaction is that when two different primers are used, the reaction conditions chosen must be such that both primers "prime" with similar efficiency. Since the two primers necessarily have different sequences, this requirement can constrain the choice of primers and require considerable experimentation. Furthermore, if one tries to amplify two different sequences simultaneously using PCR (i.e. using two sets of two probes), the reaction conditions must be optimized for four different primers.

Other known nucleic acid amplification procedures include transcription-based amplification systems (Kwoh D et al., *Proc. Natl. Acad. Sci. (U.S.A.)* 86:1173 (1989); Gingeras TR et al., PCT appl. WO 88/10315 (priority: U.S. patent applications Ser. Nos. 064,141 and 202,978)). Schemes based on litigation of two (or more) oligonucleotides in the presence of nucleic acid having the sequence of the resulting "di-oligonucleotide", thereby amplifying the di-oligonucleotide, are also known (Wu, D. Y. et al., *Genomics* 4:560 (1989)).

Miller, H. I. et al., PCT appl. WO 89/06700 (priority: U.S. patent application Ser. No. 146,462, filed Jan. 21 1988), disclose a nucleic acid sequence amplification scheme based on the hybridization of a promoter/primer sequence to a target single-stranded DNA ("ssDNA") followed by transcription of many RNA copies of the sequence. This scheme was not cyclic; i.e. new templates were not produced from the resultant RNA transcripts.

Davey, C. et al. (European Patent Application Publication no. 329,822) disclose a nucleic acid amplification process involving cyclically synthesizing single-stranded RNA ("ssRNA"), ssDNA, and double-stranded DNA (dsDNA). The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA. polymerase promoter (exemplified by T7 RNA polymerase) 5'-to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

All of the above amplification procedures depend on the principle that an end product of a cycle is functionally identical to a starting material. Thus, by repeating cycles, the nucleic acid is amplified exponentially.

Methods that use thermo-cycling, e.g. PCR or Wu, D. Y. et al., *Genomics* 4:560 (1989)), have a theoretical maximum increase of product of 2-fold per cycle, because in each cycle a single product is made from each template. In practice, the increase is always lower than 2-fold. Further slowing the amplification is the time spent in changing the temperature. Also adding delay is the need to allow enough time in a cycle for all molecules to have finished a step. Molecules that finish a step quickly must "wait" for their slower counterparts to finish before proceeding to the next step in the cycle; to shorten the cycle time would lead to skipping of one cycle by the "slower" molecules, leading to a lower exponent of amplification.

Methods that include a transcription step, e.g. that of the present invention or of Davey, C. et al. (European Patent Application Publication no. 329,822), can increase product by more than a factor of 2 at each cycle. Indeed, as 100 or more transcripts can be made from a single template, factors of increase of 100 or more are theoretically readily attainable. Furthermore, if all steps are performed under identical conditions, no molecule which has finished a particular step need "wait" before proceeding to the next step. Thus amplifications that are based on transcription and that do not require thermo-cycling are potentially much faster than thermo-cycling amplifications such as PCR.

The present invention provides an alternative method for mediating DNA amplification. In particular, it comprises an improvement over the method of Davey et al. (European Patent Application Publication no. 329,822).

SUMMARY OF THE INVENTION

The present invention concerns a method for achieving the amplification of a nucleic acid molecule. The invention achieves this goal by creating a nucleic acid molecule having a proto-promoter which is operably linked to the target sequence which is to be amplified (i.e. a "desired" sequence).

In detail, the invention provides a method of amplifying a desired nucleic acid molecule having a 3' hydroxyl terminus, which comprises the following steps in cycle:

(A) incubating the desired nucleic acid molecule in the presence of a proto-promoter-containing nucleic acid molecule, the proto-promoter-containing nucleic acid molecule having a first region complementary to a sequence present in a 3' terminal region of the desired molecule, and a second region, located 5' to the first region, and containing the proto-promoter; the incubation being under conditions sufficient to permit nucleic acid hybridization to produce a hybridized double-stranded molecule comprising the first region of the proto-promoter-containing nucleic acid molecule and the 3' terminal region of the desired molecule;

(B) incubating the hybridized molecule in the presence of an enzyme capable of extending the 3' terminus of the desired molecule in a template-dependent manner, to thereby convert the proto-promoter into a promoter capable of transcribing the desired molecule;

(C) incubating the promoter in the presence of an RNA polymerase capable of promoter-dependent transcription of the desired molecule, to thereby produce a RNA molecule complementary to the desired nucleic acid molecule (D) incubating the RNA molecule in the presence of a primer, the primer having a region complementary to a sequence present in a 3' terminal region of the RNA molecule; the incubation being under conditions sufficient to permit nucleic acid hybridization to occur and to produce a hybridized double-stranded molecule comprising the primer and the 3' terminal region of the RNA molecule; and (E) extending the primer using a template-dependent polymerase, to thereby achieve the amplification of the desired nucleic acid molecule.

The invention further provides the embodiment of the above method wherein, the promoter is a T7 promoter, and wherein the RNA polymerase is a template-dependent reverse transcriptase, or a T7 RNA polymerase.

The invention further provides the embodiment of the above method wherein the desired nucleic acid molecule is single-stranded DNA, and wherein the method is a cycle commencing with the step (A).

The invention further provides the embodiment of the above method wherein the desired nucleic acid molecule is double-stranded DNA, and wherein the method is a cycle commencing with the step (A).

The invention further provides the embodiment of the above method wherein the desired nucleic acid molecule is single-stranded RNA, and wherein the method is a cycle commencing with the step (D).

The invention further provides the embodiment of the above method wherein the desired nucleic acid molecule is double-stranded RNA, and wherein the method is a cycle commencing with the step (D).

The invention further provides a kit for amplifying a desired nucleic acid molecule, the kit being specially adapted to contain, in close compartmentalization, a first container which contains a nucleic acid molecule comprising a proto-promoter, and a second container which contains at least one primer molecule having a sequence region which is complementary to a sequence present in a 3' terminal region of a complement to the desired sequence.

The invention further provides the embodiment of the above kit which additionally contains a DNA polymerase and/or an RNA polymerase (especially T7 RNA polymerase).

DETAILED DESCRIPTION OF THE INVENTION

The present invention provides a method for amplifying a desired nucleic acid molecule in a sample. Such samples may include biological samples derived from a human or other animal source (such as, for example, blood, stool, sputum, mucus, serum, urine, saliva, teardrop, a biopsy sample, an histology tissue sample, a PAP smear, a mole, a wart, an agricultural product, waste water, drinking water, milk, processed foodstuff, air, etc.) including samples derived from a bacterial or viral preparation, as well as other samples (such as, for example, agricultural products, waste or drinking water, milk or other processed foodstuff, air, etc.).

For purposes of simplifying and illustrating the invention, representational diagrams are provided. In such illustrations, single-stranded RNA is depicted as: "≈"; single-stranded dT-containing DNA is depicted as: "—". Double-stranded nucleic acid molecules are depicted as closely positioned horizontal lines. In some illustrations, "A," "B'," or other symbols are employed to highlight a sequence region of a target molecule or primer. Such sequence regions are substantially complementary to sequences "A'," or "B'," respectively. The B' sequence can be the poly(A) tail of an mRNA. In a preferred embodiment, B is oligo(dU). The use of a deoxyuridine-containing sequence permits one to destroy the sequence, if desired, by treating the molecule in the presence of an enzyme such as UDG.

The present invention employs a variety of different enzymes to accomplish the amplification of the desired nucleic acid molecule. A "polymerase" is an enzyme that is capable of incorporating nucleoside triphosphates to extend a 3' hydroxyl group of a nucleic acid molecule, if that molecule has hybridized to a suitable template nucleic acid molecule. Polymerase enzymes are discussed in Watson, J. D., In: *Molecular Biology of the Gene,* 3rd Ed., W. A. Benjamin, Inc., Menlo Park, Calif. (1977), which reference is incorporated herein by reference, and similar texts. A preferred DNA polymerase is Taq polymerase (Cetus). Other polymerases such as the large proteolytic fragment of the DNA polymerase I of the bacterium *E. coli,* commonly known as "Klenow" polymerase, *E. coli* DNA polymerase I, and bacteriophage T7 DNA polymerase, may also be used to perform the method described herein.

The enzyme, T7 RNA polymerase, is a preferred enzyme for the transcritpitional amplification of RNA. The enzyme binds to a promoter site to mediate transcription (see, Davey et al. (European Patent Application Publication no. 329,822, herein incorporated by reference in its entirety). The present invention derives, in part, from the finding that T7 RNA polymerase is capable of binding to a double-stranded T7 promoter. Significantly, so long as the T7 promoter is double-stranded, the T7 RNA polymerase can bind to the desired nucleic acid molecule and transcribe it to form RNA. It is not necessary for the desired nucleic acid molecule to be fully double-stranded DNA; RNA transcription (from the T7 promoter using T7 RNA polymerase) will occur using a partially double-stranded DNA molecule, so long as the T7 promoter is present as double-stranded DNA (Milligan, J. F. et al., *Nucleic Acids Res.* 15:8783-8798 (1987), herein incorporated by reference in its entirety).

The term "template dependent manner" refers to nucleic acid synthesis of RNA or DNA wherein the sequence of the newly synthesized strand of nucleic acid is dictated by complementary base pairing.

When an enzymatic reaction, such as a polymerization reaction, is being conducted, it is preferable to provide the components required for such reaction in "excess" in the reaction vessel. "Excess" in reference to components of the amplification reaction refers to an amount of each component such that the ability to achieve the desired amplification is not substantially limited by the concentration of that component.

Conditions or agents which increase the rate or the extent of priming, primer elongation, or strand displacement, may increase the extent of the amplification obtained with the methods of the present invention. For instance, the addition of helicases or single-stranded nucleic acid binding proteins may increase the strand displacement rate of a DNA polymerase, or may allow the use of a DNA polymerase that might not ordinarily give substantial amplification.

It is desirable to provide to the assay mixture an amount of required cofactors such as $Mg^{++}$, and dATP, dCTP, dGTP, dTTP, ATP, CTP, GTP, UTP or other nucleoside triphosphates in sufficient quantity to support the degree of amplification desired. Nucleoside triphosphate analogues, etc. (Piccirilli, J. A. et al., *Nature* 343:33-37 (1990) can be substituted or added to those specified above, provided that the base pairing, polymerase and strand displacing functions are not adversely affected to the point that the amplification does not proceed to the desired extent.

Extension of the primer may be done with the same reverse transcriptase used to make cDNA. Alternatively, one can add a new DNA polymerase for cDNA extension. Removal of the RNA from the cDNA is preferably done by an RNase H treatment, or by the action of a helicase, but can be done by physical denaturation, e.g. heat, formamide, or alkali (high pH). In the latter case, if kinetics of renaturation are sufficiently high, this step must be followed by physical separation of the cDNA and RNA or by degradation of the RNA, e.g. by RNase or alkali. Note that sufficiently harsh alkali treatment may deaminate dC to form dU, causing a mutation.

Reverse transcription can be done with a reverse transcriptase that has RNase H activity; the use of such an enzyme is preferred over an reverse transcriptase such as an RNase H deficient polymerase such as SUPERSCRIPT TM (BRL). If one uses an enzyme having RNase H activity, it may be possible to omit a separate RNase H digestion step, by carefully choosing the reaction conditions.

All of the enzymes used in this amplification reaction, reverse transcriptase, T7 RNA polymerase, RNase H, and T4 DNA ligase, may be active under the same reaction conditions. Indeed, buffers exist in which all enzymes are near their optimal reaction conditions. Therefore, the amplification process of the present invention can be done in a single reaction volume without any change of conditions such as addition of reactants or temperature cycling. Thus, though this process has several steps at a molecular level, operationally it may have a single step. Once the reactants are mixed together, one need not add anything or change conditions, e.g. temperature, until the amplification reaction has exhausted one or more components. During this time, the nucleic acid sequence being amplified will have been increased many-fold. The level of increase will be sufficient for many purposes; however, for some purposes the reaction may have to be repeated with fresh components to achieve the desired level of amplification.

When defining conditions to be used in any specific embodiment of the present invention, there are several primer mediated, target-independent reactions, which reduce amplification efficiency, and should be examined during assay optimization. First, primers should be chosen which cannot prime on themselves or on the single-stranded portion of the proto-promoter. Second, primers can, in some cases, act as templates for T7 RNA polymerase (Sharmeen, L. et al., *Nucleic Acids Res.* 15:6705-6711 (1987)), and produce transcripts that are complementary to the primer, thereby impairing subsequent priming of RNA. Third, primers can also act as DNA templates in unusual promoter-independent transcription reactions (Krupp, G., *Nucleic Acids Res.* 17:3023-3036 (1989)). The conversion of primer into the chimeric DNA/RNA product of this reaction will significantly impair subsequent priming of RNA. Prediction of primer interactions judged solely by primer sequence analysis is often insufficient. To minimize the likelihood of potential interfering reactions, candidate primers should be tested in reactions which address each of these issues prior to their use in the amplification process. One such example is to measure the addition of nucleotides by T7 RNA polymerase to the 3' end of the candidate primer in the absence of other enzymes or DNA. Finally, in the DNA amplification scheme, a sequence which comes exclusively from the target is all that is amplified: sequences in the primer and proto-promoter are also present in amplification products. One should verify that amplification sequences do, indeed, contain target sequences, and not just proto-promoter or primer sequences.

This invention may be combined with many other processes in the arts of molecular biology to achieve a specific end. Of particular interest is purifying the target sequence from the other sequences in the nucleic acid sample. This can be accomplished most advantageously by annealing the nucleic acid sample to an oligonucleotide that is complementary to the target and is immobilized on a solid support. A convenient support would be a micro-bead, especially a magnetic micro-bead. After being so bound, the non-target sequences could be washed away, resulting in a complete or a partial purification.

After an amplification is performed, one may wish to detect any amplification products produced. Any number of techniques known to the art may be adapted to this end without undue experimentation. Particularly advantageous in some situations is the capture of RNA amplification products by a DNA oligonucleotide complementary to an RNA sequence determined by the target sequence, the oligonucleotide being bound to a solid support such as a magnetic micro-bead. Preferably, this oligonucleotide's sequence does not overlap with that of any oligonucleotide used to purify the target before the amplification. RNA:DNA hybrids thus formed may then be detected by antibodies that bind RNA:DNA heteroduplexes. Detection of the binding of such antibodies can be done by a number of methods well known to the art.

Alternatively, amplified nucleic acid can be detected by gel electrophoresis, hybridization, or a combination of the two, as is well understood in the art. Those in the art will find that the present invention can be adapted to incorporate many detection schemes.

Sequences amplified according to the methods of the invention may be purified (for example, by gel electrophoresis, by column chromatography, by affinity chromatography, by hybridization, etc.) and the fractions containing the purified products may be subjected to further amplification in accordance with the methods of the invention.

The method, provided by the present invention, for amplifying a desired nucleic acid molecule in a sample, may be used to amplify any desired nucleic acid molecule. Such molecules may be either DNA or RNA. The molecule may be homologous to other nucleic acid molecules present in the sample (for example, it may be a fragment of a human chromosome isolated from a human cell biopsy, etc.). Alternatively, the molecule may be heterologous to other nucleic acid molecules present in the sample (for example, it may be a viral, bacterial, or fungal nucleic acid molecule isolated from a sample of human blood, stools, etc.). The methods of the invention are capable of simultaneously amplifying both heterologous and homologous molecules. For example, amplification of a human tissue sample infected with a virus may result in amplification of both viral and human sequences.

"Amplification" as used herein refers to an increase in the amount of the desired nucleic acid molecule present in a sample. "Substantial amplification" refers to greater than about three-fold amplification.

A "Sequence Region" is a conceptual aid for illustrating the methods of the present invention. A "Sequence Region" is merely a sequence of nucleotides contained within the total nucleotide sequence of the desired molecule that exhibits a feature or attribute which is employed, in accordance with the present invention, to achieve the amplification of the desired molecule. Unless specified, the particular nucleotide sequence of a Sequence Region need not be known in order to amplify the desired nucleic acid molecule. Examples of sequence regions include proto-promoter containing regions, sequence regions capable of binding to such regions, etc.

As used herein, two sequences are said to be able to hybridize to one another if they are capable of forming an anti-parallel double-stranded nucleic acid structure. Conditions of nucleic acid hybridization suitable for forming such double stranded structures are described by Maniatis, T., et al. (In: *Molecular Cloning, A Laboratory Manual,* Cold Spring Harbor Laboratories, Cold Spring Harbor, N.Y. (1982)), and by Haymes, B. D., et al. (In: *Nucleic Acid Hybridization, A Practical Approach,* IRL Press, Washington, D.C. (1985)). Two sequence are said to be "complementary" to one another if they are capable of hybridizing to one another to form a stable anti-parallel double-stranded nucleic acid structure. Thus, the sequences need not exhibit precise complementarity, but need only be sufficiently complementary in sequence to be able to form a stable double-stranded structure. Thus, departures from complete complementarity are permissible, so long as such departures are not sufficient to completely preclude hybridization to form a double-stranded structure.

The present methods do not require that the molecules to be amplified have any particular sequence or length. In particular, the molecules which may be amplified include any naturally occurring procaryotic (for example, pathogenic or non-pathogenic bacteria, Escherichia, Salmonella, Clostridium, Agrobacter, Staphylococcus and Streptomyces, Streptococcus, Rickettsiae, Chlamydia, Mycoplasma, etc.), eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid. The nucleic acid molecule can also be any nucleic acid molecule which has been or can be chemically synthesized. Thus, the nucleic acid sequence may or may not be found in nature.

The desired nucleic acid molecule which is to be amplified may be in either a double-stranded or single-stranded form. However, if the nucleic acid is double-stranded at the start of the amplification reaction it is preferably first treated to render the two strands into a single-stranded, or partially single-stranded, form. Methods are known to render double-stranded nucleic acids into single-stranded, or partially single-stranded, forms, such as heating, or by alkali treatment, or by enzymatic methods (such a by helicase action, etc.), or by binding proteins, etc. General methods for accomplishing this treatment are provided by Maniatis, T., et al. (In: *Molecular Cloning, A Laboratory Manual,* Cold Spring Harbor Laboratories, Cold Spring Harbor, N.Y. (1982)), and by Haymes, B. D., et al. (In: *Nucleic Acid Hybridization, A Practical Approach,* IRL Press, Washington, D.C. (1985)), which references are herein incorporated by reference.

Macromolecular entities that contain nucleic acid other than double-stranded DNA, or single-stranded DNA, such as single-stranded RNA, double-stranded RNA or mRNA are capable of being amplified by the method of the invention. For example, the RNA genomes of certain viruses can be converted to DNA by reaction with enzymes such as reverse transcriptase (Maniatis, T. et al., *Molecular Cloning (A Laboratory Manual)*, Cold Spring Harbor Laboratory, 1982; Noonan, K. F. et al., *Nucleic Acids Res.* 16:10366 (1988)). The product of the reverse transcriptase reaction may then be amplified according to the invention.

Figure 1:
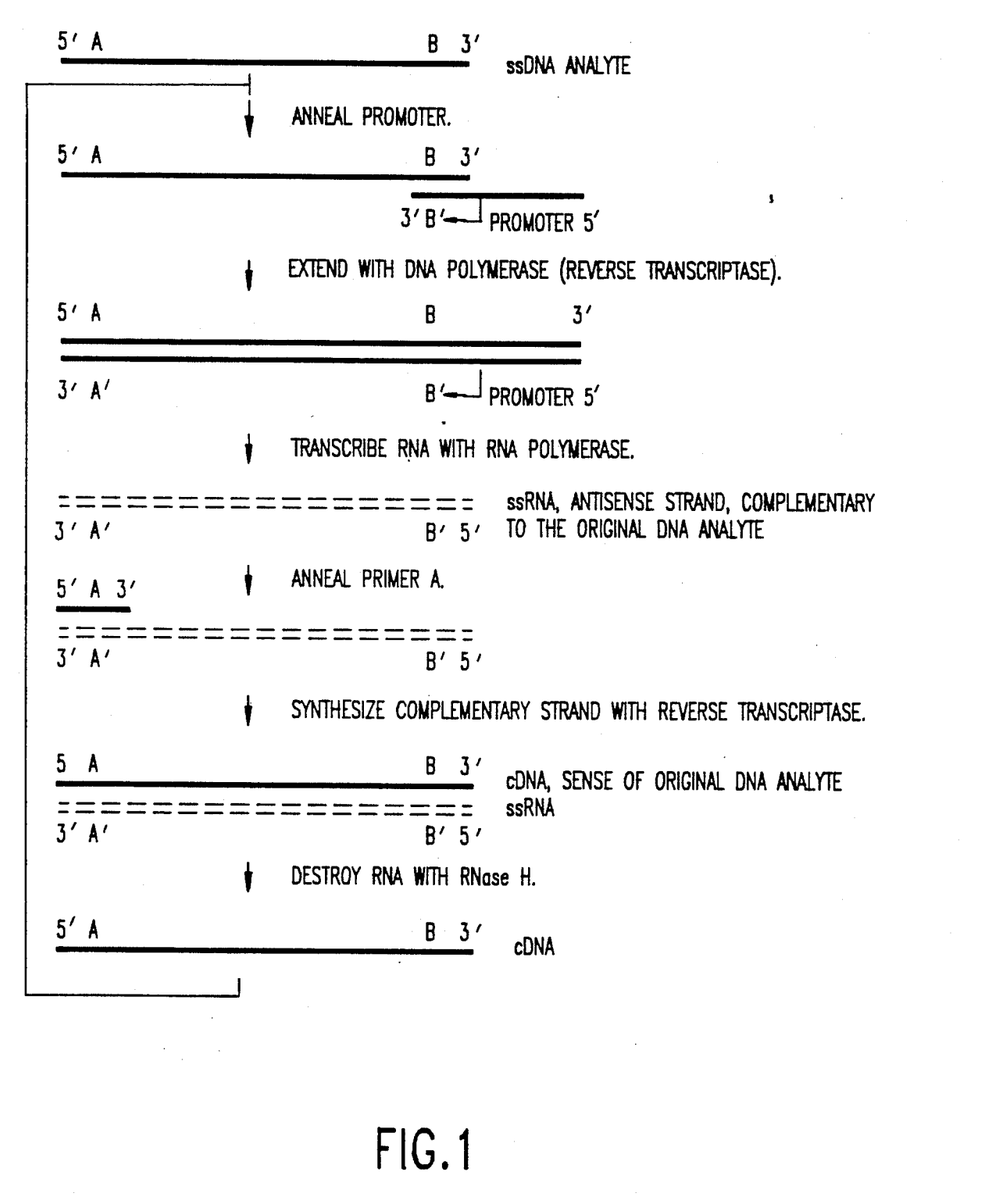
FIG. 1 depicts the method used by Davey, C. et al. to amplify a ssDNA molecule.
Figure 2:
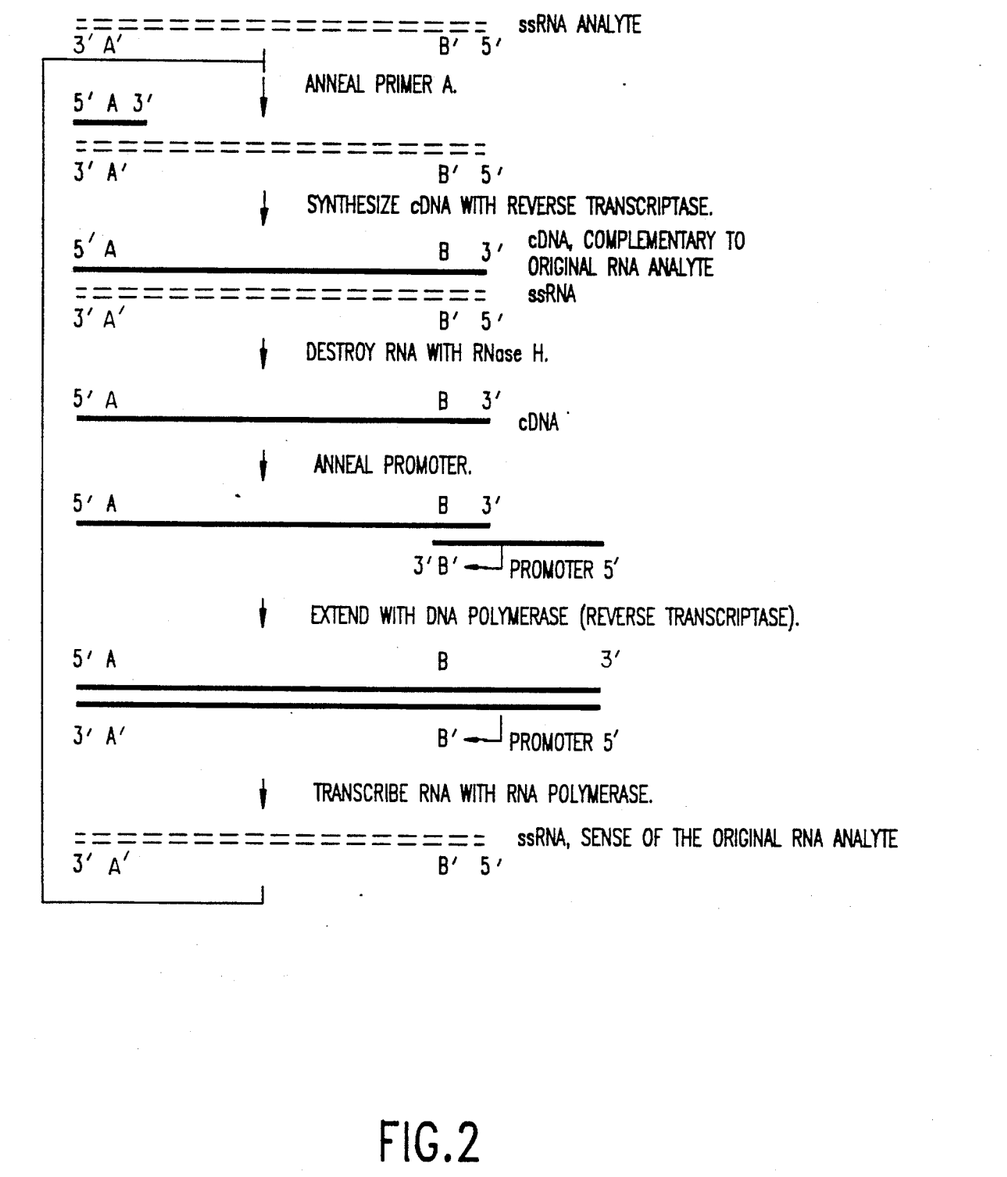
FIG. 2 depicts the method used by Davey, C. et al. to amplify an RNA molecule.

The present invention is an improvement over that described by Davey, C. et al. (European Patent Application Publication no. 329,822). In order to illustrate the methods of the present invention, such methods are compared to those used by Davey, C. et al. to amplify a ssDNA or an RNA "desired nucleic acid molecule."

The method used by Davey, C. et al. to amplify a ssDNA molecule is depicted in FIG. 1. The method used by Davey, C. et al. to amplify an RNA molecule is depicted in FIG. 2.

As will be appreciated, a key attribute of the method described by Davey, C. et al. for amplifying a ssDNA molecule is the use of a DNA polymerase, such as reverse transcriptase to extend the hybridized primer until a double-stranded molecule is created. The method then amplifies this double-stranded molecule.

Similarly, in the method described by Davey, C. et al. for amplifying an RNA molecule, a reverse transcriptase is used to produce a cDNA molecule complementary to the RNA molecule. This molecule forms a cDNA::RNA double-stranded molecule, which is then amplified by the method to form a double-stranded DNA molecule. The method then amplifies this double-stranded molecule.

As discussed above, T7 RNA polymerase is capable of transcribing a single-stranded template (provided that the T7 promoter region is double-stranded). The present invention exploits this characteristic through the use of a hybridizing nucleic acid molecule. The molecule has a sequence region which is capable of specifically hybridizing to a sequence region present in the desired DNA or RNA molecule which is to be amplified. The molecule additionally possesses a sequence region which is a T7 proto-promoter region. A proto-promoter is a single-stranded DNA or RNA sequence region which, in double-stranded form is capable of mediating RNA transcription. The most preferred proto-promoter is a single-stranded sequence which contains the T7 promoter (Milligan, J. F. et al., *Nucleic Acids Res.* 15:8783–8798 (1987)). This proto-promoter is substantially incapable of mediating transcription unless first rendered double-stranded (thereby forming a promoter). The hybridizing sequence region will preferably be located 3′ to the proto-promoter sequence region. Significantly, the 3′ terminus of the molecule is blocked, and thus is incapable of serving as a substrate for primer extension reactions. The 3′ terminus may be blocked through, for example, the use of a 3′ terminal nucleotide lacking a 3′ hydroxyl group (e.g. 3′ deoxyadenosine, etc.)

When such a nucleic acid molecule hybridizes to a linear or linearized desired molecule having a 3′ hydroxyl terminus, the 3′ terminus can be extended to thereby produce an extended desired molecule which contains a sequence complementary to that of the proto-promoter region of the nucleic acid molecule. These complementary sequences will hybridize to one another, to thereby form a promoter. The promoter will direct the template-dependent transcription of the desired molecule. This step of the method produces substantial amounts of the complement of the desired nucleic acid molecule.

To amplify the desired molecule, a primer molecule is added which is capable of hybridizing to the 3′ terminus region of the transcribed RNA. The 3′ terminus of the primer molecule is unblocked, and thus is capable of serving as a substrate for the template-dependent formation of cDNA. This step of the method produces one copy of the desired nucleic acid molecule for every copy of the complement molecule produced in the prior step.

Figure 3:
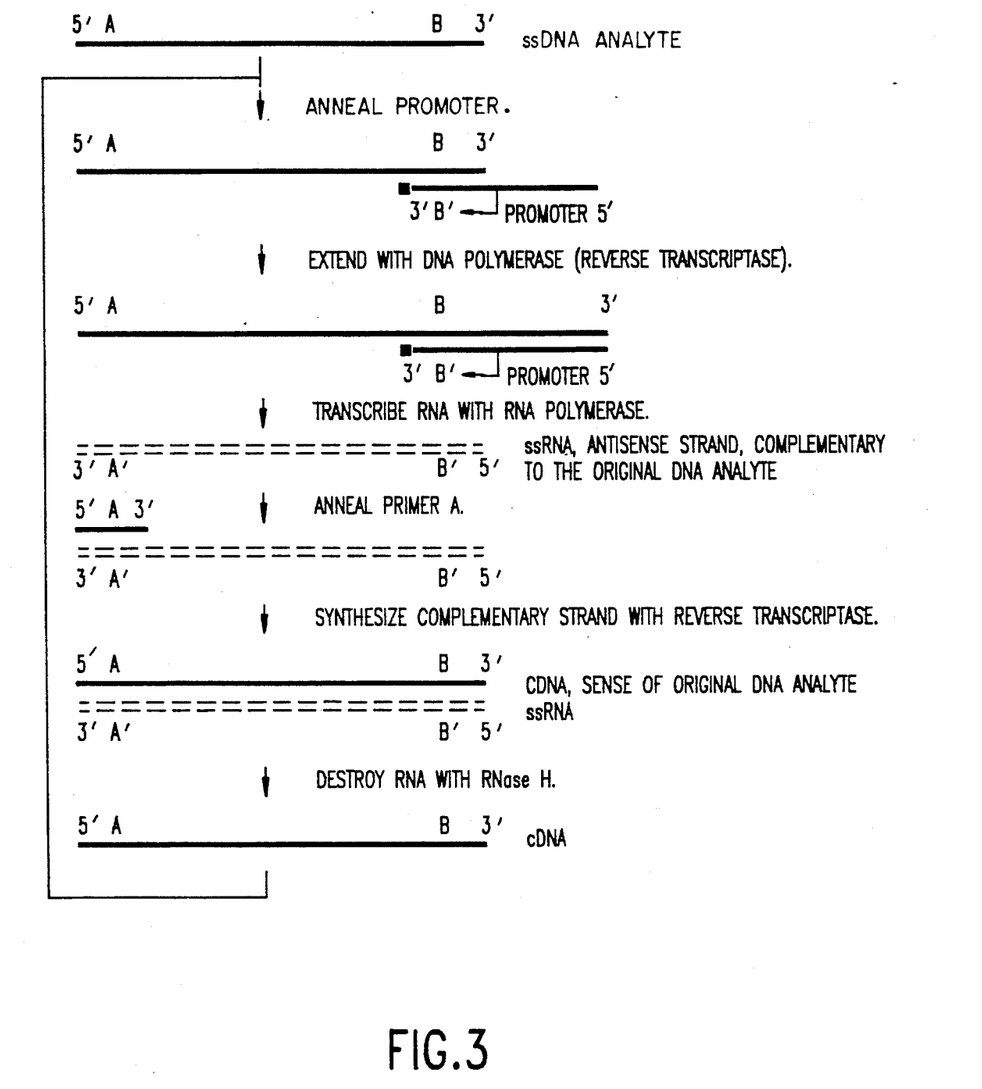
FIG. 3 illustrates how the present invention accomplishes the amplification of an RNA molecule.

Thus, the present invention accomplishes the amplification of a DNA molecule as illustrated in FIG. 3 (the symbol " " denotes that the 3′ terminus of a molecule is blocked).

Figure 4:
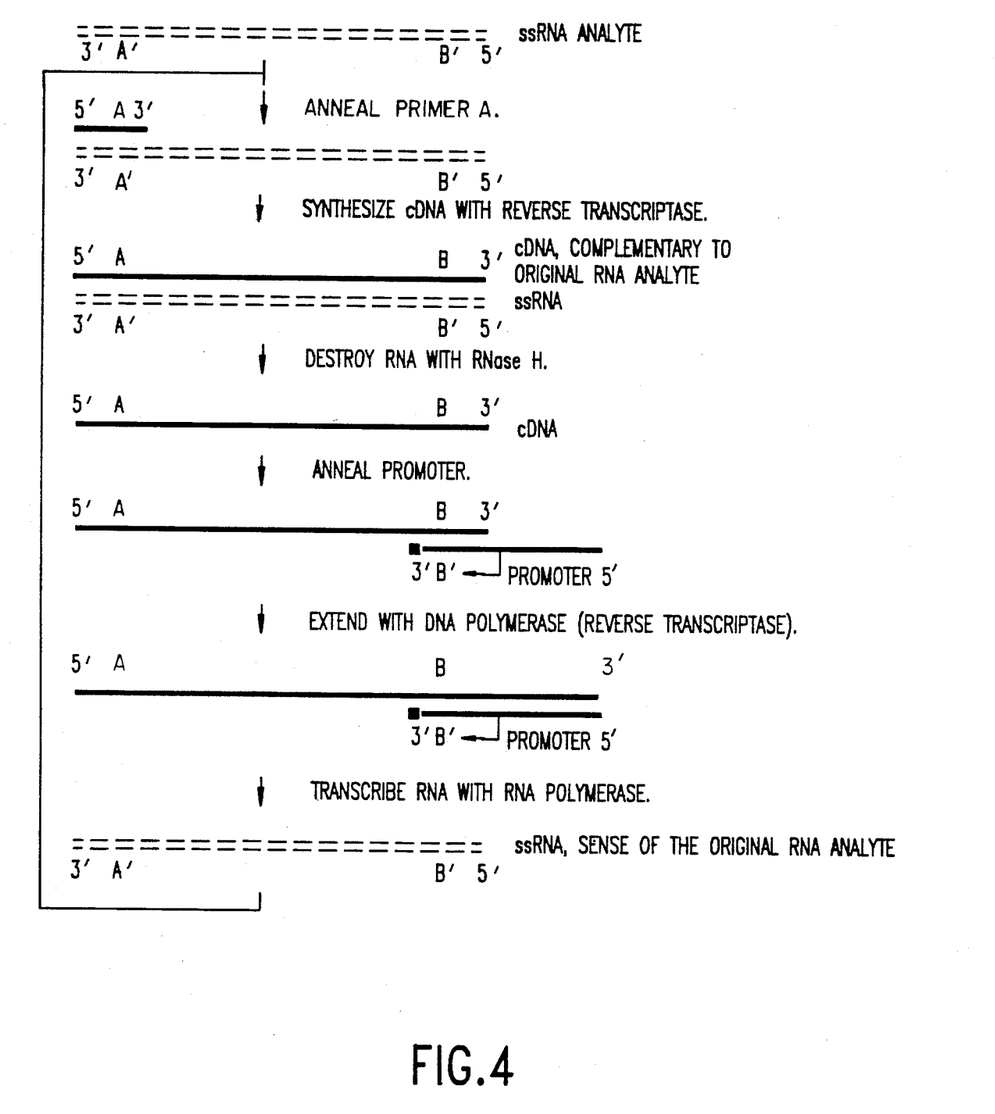
FIG. 4 illustrates how the present invention accomplishes the amplification of an RNA molecule.

Similarly, the present invention accomplishes the amplification of an RNA molecule as illustrated in FIG. 4 (the symbol "■" denotes that the 3′ terminus of a molecule is blocked).

As will be appreciated, a nucleic acid molecule of unknown sequence may possess regions whose sequences are capable of forming a secondary structure that may impede or block the action of a DNA polymerase or reverse transcriptase. Similarly, such nucleic acid molecules may have internal proto-promoters. The formation of a double-stranded DNA molecule might serve to permit such promoters to mediate transcription and thus impair the amplification procedure. As will be perceived, these drawbacks of the method of Davey et al. are averted through the use of the methods of the present invention.

The present invention includes articles of manufacture, such as "kits." In one embodiment, such kits will, typically, be specially adapted to contain in close compartmentalization a first container which contains a nucleic acid molecule comprising a proto-promoter, and a second container which contains at least one primer molecule having a sequence region which is complementary to a sequence present in a 3′ terminal region of a complement to the desired sequence. The kit may also, optionally, contain one or more DNA and/or RNA polymerases, buffers, etc. in amounts sufficient to permit the amplification of a desired nucleic acid molecule. The kit may additionally contain instructional brochures, and the like.

Having now generally described the invention, the same will be more readily understood through reference to the following examples which are provided by way of illustration, and are not intended to be limiting of the present invention, unless specified.

EXAMPLE 1

Amplification of a Nucleic Acid Sequence of an RNA Molecule

Materials and Methods

Reagents

Oligonucleotides were synthesized by cyanoethyl-phosphoramidite chemistry using an Applied Biosystems 380A DNA synthesizer. Reagents used for syntheses were purchased from Cruachem. Oligonucleotides were purified by denaturing polyacrylamide gel electrophoresis. DNA was eluted from the gel matrix in 20 mM Tris-HCl (pH 8.0), 0.5M ammonium acetate, 1 mM EDTA, 0.01% sodium dodecyl sulfate at 37° C. for 16 hours, and then desalted by molecular exclusion chromatography using PD-10 columns from Pharmacia. Proto-promoter oligonucleotide was constructed with a blocked 3' terminus using a cordycepin modified CPG column for oligonucleotide synthesis.

Enzymes used for the amplification procedure (T7 RNA polymerase, *E. coli* RNase H, Superscript ™ RNase H⁻ Reverse Transcriptase) were obtained from Life Technologies, Inc./ BRL. RNasin ribonuclease inhibitor was from Promega. Deoxyribonucleoside triphoshates (dATP, dCTP, dGTP, and dTTP) and ribonucleoside triphosphates (ATP, CTP, GTP, and UTP) were purchased from Pharmacia as 100 mM solutions. Biochemicals used for buffer components were from Sigma.

Preparation of RNA Analyte

A DNA segment from the L1 region of Human Papilloma Virus (HPV) type 16 was cloned into plasmid vector pT71 (USB) behind a T7 RNA Polymerase promoter. In vitro transcription was performed using T7 RNA polymerase (BRL, 12,000 U) and 10 µg of plasmid template in the presence of inorganic pyrophosphatase (ICN, 25 U) and Human Placental RNase Inhibitor (Promega, 200 U) in a 1 ml reaction. The reaction was incubated for 60 min at 37° C., then extracted once using a 50:50 mixture of phenol:chloroform. The DNA template was degraded using RNase-free DNase (BRL). The RNA transcript was purified by G-50 (Pharmacia) size exclusion column chromatography. Equilibration and elution buffer was TE containing 100 mM NaCl and 0.1% SDS.

Amplification

Amplification reactions were performed in 25 µl volumes of 50 mM Tris-HCl (pH 8.3), 175 mM potassium glutamate, 6% polyethyleneglycol 8000, 6 mM $MgCl_2$, 10 mM DTT, 1 mM ATP, 1 mM CTP, 1 mM GTP, 1 mM UTP, 250 µM dATP, 250 µM dCTP, 250 µM dGTP, 250 µM dTTP, 0.5 µM cDNA primer oligonucleotide, 0.2 µM of a T7-promoter-containing template oligonucleotide, 400 units T7 RNA polymerase, 150 units Superscript ™ RNase H(−) M-MLV reverse transcriptase, 0.05 units *E. coli* ribonuclease H, and 20 units RNasin ribonuclease inhibitor. Reaction mixtures were prepared on ice, RNA analyte sequence added, and then incubated at 37° C. for 3 hours. Reactions were performed with either 0, 10, 100, 1,000, 10,000, or 100,000 molecules of RNA analyte sequence in a background of 100 ng total RNA prepared from HTB31 cells. Amplification was terminated by addition of an equal volume of 50 mM EDTA to each reaction.

Analysis

Amplification products were assayed by dot-blot hybridization with a $^{32}P$-labelled oligonucleotide probe specific for the RNA produced by the procedure. Amplification products (1/10$^{th}$ volume from each reaction) and serial dilutions of the RNA analyte (used as hybridization standards) were denatured by reaction with glyoxal, essentially as described by Carmichael and McMaster (*Met. Enzymol.* 65:380–391 (1980)), then immobilized to Biodyne B nylon membrane (Pall) in 20X SSC with a 96 well manifold (Bio-Rad Laboratories, Richmond, Calif.) according to the manufacturer's instructions. Filters were baked at 80° C. for 0.5 hours, followed by UV fixation on a 302 nm transilluminator for 2 minutes.

The oligonucleotide probe was labeled with $^{32}P$ by the kinase reaction to a specific activity of $1-2 \times 10^8$ dpm/µg using a 5' DNA Terminus Labeling System (Life Technologies, Inc./BRL) according to the manufacturer's recommendations. Probe was purified by gel filtration with Sephadex G-50 (Pharmacia LKB Biotechnology Inc.).

Dot-blot membrane was pre-hybridized for 30 minutes in 1M NaCl, 30% formamide, 50 mM sodium phosphate (pH 7.4), 1 mM EDTA, 0.1% gelatin, 50 g/ml yeast tRNA, and 5% SDS at 42° C. Hybridization was performed at 42° C. with fresh hybridization solution containing $1 \times 10^7$ dpm/ml probe for 16 hours. Following hybridization, the filter was washed 5 times for 5 minutes at 42° C. with 0.1X SSC, 0.1%SDS then autoradiographed at −70° C. using Kodak XAR-RP film and a Quanta III intensifying screen (Dupont).

Comparison of relative signal intensity between hybridization to serial dilutions of the RNA analyte sequence (hybridization standards) and RNA amplification products resulting from predetermined concentrations of target input was used to determine the efficiency of amplification achieved during the procedure.

Results

Target amplification exceeded $1 \times 10^7$ fold and dose response was roughly linear from $10^2$ to $10^5$ input molecules. Hybridization signal resulting from amplification reactions containing 100 target molecules were roughly 5 fold greater than that produced by controls lacking target and slightly more intense than that of the $10^9$ molecule hybridization standard.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of amplifying a desired nucleic acid molecule having a 3' hydroxyl terminus, which comprises the following steps in cycle:
 (A) incubating said desired nucleic acid molecule in the presence of a nucleic acid molecule comprising a proto-promoter, said proto-promoter being a single-stranded sequence region which, in double-stranded form is capable of mediating RNA transcription, said proto-promoter-containing nucleic acid molecule having a first region complementary to a sequence present in a 3' terminal region of said desired molecule, and a second region, located 5' to said first region, and containing said proto-promoter; said proto-promoter-containing nucleic acid molecule additionally having a 3' terminus that is incapable of being extended by a polymerase; said incubation being under conditions sufficient to permit nucleic acid hybridization to produce a hybridized double-stranded molecule comprising said first region of said proto-promoter-containing nucleic acid molecule and said 3' terminal region of said desired molecule;

(B) incubating said hybridized molecule in the presence of an enzyme capable of extending the 3' terminus of said desired molecule in a template-dependent manner, to thereby convert said proto-promoter into a promoter capable of transcribing said desired molecule;

(C) incubating said promoter in the presence of an RNA polymerase capable of promoter-dependent transcription of said desired molecule, to thereby produce a RNA molecule complementary to said desired nucleic acid molecule;

(D) incubating said RNA molecule in the presence of a primer, said primer having a region complementary to a sequence present in a 3' terminal region of said RNA molecule; said incubation being under condition sufficient to permit nucleic acid hybridization to occur and to produce a hybridized double-stranded molecule comprising said primer and said 3' terminal region of said RNA molecule; and (E) extending said primer using a template-dependent polymerase, to thereby achieve the amplification of said desired nucleic acid molecule.

2. The method of claim 1, wherein said promoter is a T7 promoter.

3. The method of claim 1, wherein said polymerase is a template-directed reverse transcriptase.

4. The method of claim 1, wherein said desired nucleic acid molecule is single-stranded DNA, and wherein said method, in its entirety, is a cycle commencing with said step (A).

5. The method of claim 1, wherein said desired nucleic acid molecule is double-stranded DNA, and wherein said method, in its entirety, is a cycle commencing with step (A).

6. The method of claim 1, wherein said desired nucleic acid molecule is single-stranded RNA, and wherein said method, in its entirety, is a cycle commencing with said step (D).

7. The method of claim 1, wherein said desired nucleic acid molecule is double-stranded RNA, and wherein said method, in its entirety, is a cycle commencing with said step (D).

8. The method of claim 2, wherein said RNA polymerase is T7 RNA polymerase.

9. A kit for amplifying a desired nucleic acid molecule, said kit containing, in close compartmentalization, a first container which contains a nucleic acid molecule comprising a proto-promoter, said proto-promoter being a single-stranded sequence region which, in double-stranded form is capable of mediating RNA tranzscription and wherein said proto-promoter-containing nucleic acid molecule additionally possesses a 3' terminus that is incapable of being extended by a polymerase, and a second container which contains at least one primer molecule having a sequence region which is complementary to a sequence present in a 3' terminal region of a complement of the desired sequence.

10. The kit of claim 9 which additionally contains a DNA polymerase.

11. The kit of claim 9 which additionally contains a RNA polymerase.

12. The kit of claim 11 wherein said RNA polymerase is T7 polymerase.

13. The kit of claim 10 wherein said DNA polymerase is a reverse transcriptase.

* * * * *